United States Patent
Pulsifer

(10) Patent No.: US 7,066,328 B2
(45) Date of Patent: Jun. 27, 2006

(54) GROOVED ANGLED TRAY FOR RING-HANDLED SURGICAL INSTRUMENTS

(76) Inventor: Janice Pulsifer, One Irving St., Cranston, RI (US) 02910-1422

( * ) Notice: Subject to any disclaimer, the term of this patent is extended or adjusted under 35 U.S.C. 154(b) by 57 days.

(21) Appl. No.: 10/840,398

(22) Filed: May 7, 2004

(65) Prior Publication Data

US 2005/0040066 A1    Feb. 24, 2005

Related U.S. Application Data

(60) Provisional application No. 60/496,928, filed on Aug. 22, 2003.

(51) Int. Cl.
*B65D 83/10* (2006.01)
(52) U.S. Cl. ................. 206/363; 206/372; 206/564
(58) Field of Classification Search ............... 206/214, 206/372, 373, 349, 363, 364, 365, 366, 370, 206/561, 564, 438; 211/70.6; D24/227
See application file for complete search history.

(56) References Cited

U.S. PATENT DOCUMENTS

| | | | |
|---|---|---|---|
| 25,839 A * | 10/1859 | Allen .......................... 19/295 |
| 3,868,016 A | 2/1975 | Szpur et al. | |
| 4,011,944 A | 3/1977 | Cooley et al. | |
| 4,046,254 A | 9/1977 | Kramer | |
| D248,871 S | 8/1978 | Forsman et al. | |
| D249,362 S | 9/1978 | Forsman et al. | |
| 4,229,420 A | 10/1980 | Smith et al. | |
| D262,824 S | 1/1982 | Diguan | |
| 4,342,391 A | 8/1982 | Schainholz | |
| D269,791 S * | 7/1983 | Chatham ..................... D19/77 |
| D276,462 S | 11/1984 | Villarreal | |
| 4,512,466 A | 4/1985 | Delang | |
| 4,577,755 A | 3/1986 | Ramsay | |
| D288,482 S * | 2/1987 | Blatherwick et al. ...... D24/230 |
| 4,993,583 A * | 2/1991 | Chasen ....................... 220/482 |
| 5,005,590 A | 4/1991 | Eldridge, Jr. et al. | |
| 5,046,624 A | 9/1991 | Murphy et al. | |
| 5,059,271 A | 10/1991 | Taub | |
| 5,097,963 A * | 3/1992 | Chernosky et al. ......... 211/60.1 |
| 5,137,151 A | 8/1992 | Choate | |
| D329,876 S * | 9/1992 | Breen ......................... D19/75 |
| 5,170,804 A | 12/1992 | Glassman | |
| 5,195,538 A | 3/1993 | Eldridge, Jr. et al. | |
| 5,363,862 A * | 11/1994 | Mercier ....................... 128/846 |
| 5,449,069 A * | 9/1995 | Pijanowski et al. ......... 206/370 |
| D368,532 S * | 4/1996 | Jonkman et al. ........... D24/227 |

(Continued)

FOREIGN PATENT DOCUMENTS

GB          2 360 759 A       10/2001

*Primary Examiner*—Shian T. Luong
(74) *Attorney, Agent, or Firm*—Richard C. Litman

(57) ABSTRACT

The grooved angled tray for ring-handled surgical instruments includes a horizontal top, a horizontal base that is disposed parallel to the horizontal top, a front wall, a rear wall, and a set of parallel sidewalls. The front wall is inclined and slopes outward from the top. The horizontal top and the front wall are adapted to hold and isolate a variety of ring-handled instruments. The horizontal top is provided with a series of grooves that receive the ring handles of the ring-handled instruments. The front wall has an inclined ramp that allows lower portions of the ring-handled instruments to rest. In another embodiment, the horizontal top and front wall are together provided with a series of grooves that receive the ring handles and the lower portions of the ring-handled instruments.

5 Claims, 6 Drawing Sheets

U.S. PATENT DOCUMENTS

| | | | |
|---|---|---|---|
| D377,951 S * | 2/1997 | McDiarmid | D19/78 |
| 5,791,472 A | 8/1998 | Davis | |
| 5,848,693 A | 12/1998 | Davis et al. | |
| 6,158,437 A | 12/2000 | Vagley | |
| D438,634 S * | 3/2001 | Merry | D24/227 |
| 6,216,885 B1 | 4/2001 | Guillaume | |
| 6,405,863 B1 | 6/2002 | Dhindsa | |
| 6,426,041 B1 | 6/2002 | Smith | |
| D464,887 S * | 10/2002 | Sherwell | D9/516 |
| D471,641 S | 3/2003 | McMichael et al. | |
| 2001/0035384 A1 | 11/2001 | Davis et al. | |
| 2002/0074253 A1 | 6/2002 | Allen et al. | |

* cited by examiner

GROOVED ANGLED TRAY FOR RING-HANDLED SURGICAL INSTRUMENTS

CROSS-REFERENCE TO RELATED APPLICATION

This application claims the benefit of U.S. Provisional Patent Application Ser. No. 60/496,928, filed Aug. 22, 2003.

BACKGROUND OF THE INVENTION

1. Field of the Invention

The present invention relates to a device for organizing surgical instruments, and particularly, to a surgical instrument tray useful for organizing ring-handled instruments.

2. Description of the Related Art

Ring-handled surgical instruments are normally separated and organized during surgical procedures and also prior to sterilization by being laid out on rolled-up cotton towels. The rolled-up cotton towels, which may have their outside edges taped, support the instruments such that the instruments can be more easily counted, selected and handled by a nurse or surgical technician. Generally, the technician or nurse grips the instruments on the lower portions of the instruments and places the ring handles of the instrument directly into the doctor's hand during operation.

Such rolled cotton towels, with the surgical instruments supported thereon, are usually laid out on a tray or a table. Sometimes, however, before and during use of the surgical instruments, the instruments supported on the rolled towel can become mixed and disorganized. Accordingly, the instruments become more difficult to count, select and handle prior to actual use of the instruments, or while the instruments are assembled prior to sterilization.

A few instrument stands, racks and trays are recognized in the prior art, but none provide a compact, inexpensive, and efficient manner in which to space and stack ring-handled surgical instruments.

U.S. Pat. No. 6,426,041 B1, issued Jul. 30, 2002, discloses a surgical instrument tray that can hold and display about one hundred ring-handled surgical instruments that are held and displayed in a perpendicular fashion. The tray has recesses of varying shape and size to accommodate certain instruments.

U.S. Pat. No. 5,046,624, issued Sep. 10, 1991, to S. Murphy et al., discloses a surgical instrument stand. The stand includes an elongated rectangular body and vertical compartments formed within the body for holding ring-handled surgical instruments.

U.S. Pat. No. 4,577,755, issued Mar. 25, 1996 to M. Ramsay, discloses a surgical instrument tray having a base with a raised portion to support lever members of ring-handled surgical instruments. The base is formed to have an end portion angulating away from the base with slots formed therein sized to receive the ring handles in order to hold the instruments.

Other patents showing surgical instrument trays include U.S. Pat. No. 6,405,863 B1, issued Jun. 18, 2002 to A. S. Dhindsa (system for organizing set of surgical instruments for endoscopic surgical procedure); U.S. Pat. No. 6,216,885 B1, issued Apr. 17, 2001 to C. Guillaume (a tray for grouping together medical instruments); U.S. Pat. No. 6,158,437, issued Dec. 12, 2000 to R. T. Vagley (method of performing a surgical procedure and associated surgical instrument for support tray); U.S. Pat. No. 5,848,693, issued Dec. 15, 1998 to Davis et al. (laparoscopic surgical tray with apertured clips); U.S. Pat. No. 5,791,472, issued Aug. 11, 1998 to M. S. Davis (surgical tray for sharp surgical instruments); U.S. Pat. No. 5,195,538, issued Mar. 23, 1993 to J. Eldridge, Jr. et al. (surgical instrument tray).

Additional patents showing surgical instrument trays include U.S. Pat. No. 5,170,804, issued Dec. 15, 1992 to J. Glassman (Mayo stand disposable drape); U.S. Pat. No. 5,137,151, issued Aug. 11, 1992 to C. A. Choate (instrument rack for supporting a plurality of instruments); U.S. Pat. No. 5,097,963, issued Mar. 24, 1992 to Chernosky et al. (sterile protective system for surgical instruments during a surgical operation); U.S. Pat. No. 5,059,271, issued Oct. 22, 1991 to S. Taub (method of supporting and retaining surgical instruments on a non-skid supporting surface); U.S. Pat. No. 5,005,590, issued Apr. 9, 1991 to J. Eldridge, Jr. et al. (surgical instrument tray); U.S. Pat. No. 4,512,466, issued Apr. 23, 1985 to T. G. Delang (surgical instrument organizer); U.S. Pat. No. 4,342,391, issued Aug. 3, 1982 to H. Schainholz (instrument count memorizer); U.S. Pat. No. 4,229,420, issued Oct. 21, 1980 to G. F. Smith et al. (surgical instrument rack); U.S. Pat. No. 4,046,254, issued Sep. 6, 1977 to S. Kramer (surgical trays); U.S. Pat. No. 4,011,944, issued Mar. 15, 1977 to D. A. Cooley et al. (disposable surgical equipment tray); U.S. Pat. No. 3,868,016, issued Feb. 25, 1975 to R. Szpur (magnetized surgical instrument tray restraint).

Further patents showing surgical instrument trays include U.S. Pat. Pub. No. US 2002/0074253 A1, published Jun. 20, 2002 and invented by K. Allen et al. (tray for medical instrumentation); U.S. Pat. Pub. No. 2001/0035384 A1, published Nov. 1, 2001 and invented by Davis et al. (instrument organizer with movable stabilizing post); U.S. Pat. No. U.S. 471,641 S, issued Mar. 11, 2003 to D. McMichael et al. (surgical kit tray); U.S. Pat. No. Des. 276,462, issued Nov. 20, 1984 to I. Villarreal (surgical instrument tray) U.S. Pat. No. Des. 262,824, issued Jan. 26, 1982 to B. Diguan (surgical tray for ophthalmic instruments); U.S. Pat. No. Des. 249,362, issued Sep. 12, 1978 to T. Forsman et al. (surgical instrument tray); U.S. Pat. No. Des. 248,871, issued Aug. 8, 1978 to T. Forsman et al. (surgical instrument tray); and UK Patent No. GB 2 360 759 A, published Oct. 3, 2001 (surgical instrument tray with removable lid).

None of the above inventions and patents, taken either singly or in combination, is seen to describe the instant invention as claimed. Thus a grooved angled tray for ring-handled surgical instruments solving the aforementioned problems is desired.

SUMMARY OF THE INVENTION

The grooved angled tray for ring-handled surgical instruments includes a horizontal top, a horizontal base that is disposed parallel to the horizontal top, a front wall, a rear wall, and a set of parallel sidewalls. The front wall is inclined and slopes outward from the top. The horizontal top and the front wall provide an area into which the ring-handled instruments are placed. In one embodiment, the horizontal top is disposed slightly lower than the front wall and is provided with grooves that are adapted to hold and isolate only the ring handles of the ring-handled instruments. The front wall contains a ramp that holds the lower portions of the ring-handled instruments. In another embodiment, the horizontal top and the front wall are provided jointly with a series of specially configured grooves that are adapted to hold and isolate a variety of ring-handled instruments.

One sidewall contains a pair of locking members along the horizontal base. The locking members allow the grooved angled tray to lock onto an additional grooved angled tray.

Accordingly, it is a principal aspect of the invention to provide a grooved angled tray for ring-handled surgical instruments that maintains ring-handled surgical instruments in a slanted parallel position.

It is another aspect of the invention to provide a grooved angled tray for ring-handled surgical instruments that facilitates counting of the ringed instruments during surgical procedures.

It is a further aspect of the invention to provide a grooved angled tray for ring-handled surgical instruments that provides a stable surface upon which to mount the instruments.

It is an additional aspect of the invention to provide a grooved angled tray for ring-handled surgical instruments that allows the instruments to be easily grasped at the lower portions of the instruments prior to transfer into the doctor's hands.

It is an aspect of the invention to provide improved elements and arrangements thereof for the purposes described which is inexpensive, dependable and fully effective in accomplishing its intended purposes.

These and other aspects of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENT

Figure 1:
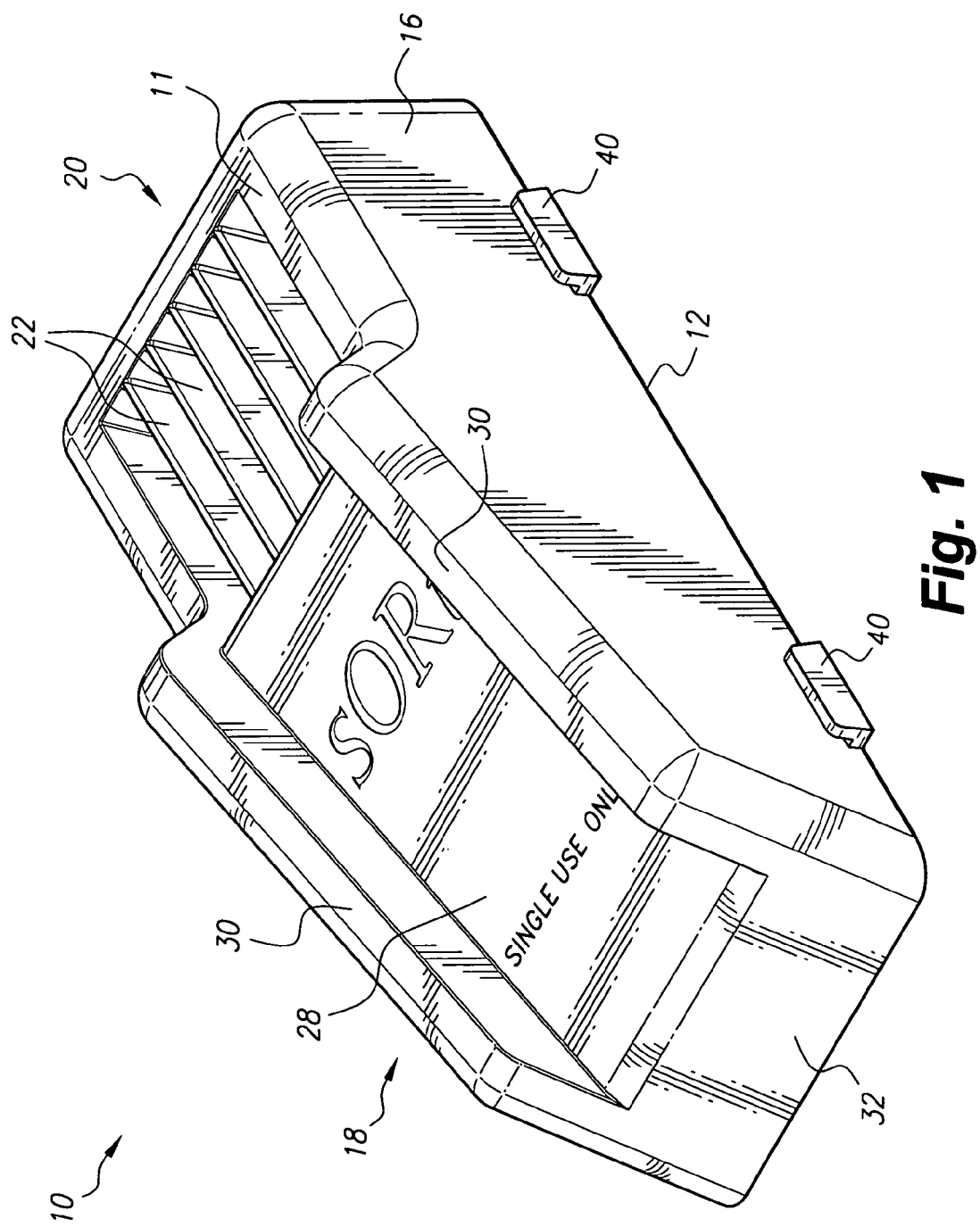
FIG. 1 is a perspective view of a grooved angled tray for ring-handled surgical instruments according to a first embodiment of the present invention.

The present invention relates to a grooved angled tray for ring-handled surgical instruments, designated generally as 10 in the drawings. The tray 10 can be made in various shapes and sizes. The tray 10 includes a horizontal top 11, a horizontal base 12 parallel to the horizontal top 11, a sloped front wall 18, a rear wall 20, and parallel, opposing sidewalls 16. The rear wall 20 is vertical and extends normal to the top 11 and base 12. The front wall 18 slopes downward and extends to the base 12. The horizontal top 11 and the front wall 18 provide space into which ring-handled instruments are placed.

Referring first to FIG. 1, the tray 10 is shown with grooves 22 situated within the horizontal top 11 and an inclined ramp 28 along the front wall 18. The horizontal top 11 is disposed lower than the front wall 18. The grooves 22 in the horizontal top 11 allow for placement of a portion of the ring handles of the ring-handled instruments. The front wall 18 includes an inclined ramp 28 situated between a set of ramp sidewalls 30. The ramp 28 allows lower portions of the ring-handled instruments to rest. The front wall 18 angles slightly downward, then at the end of the inclined ramp 28, a bottom portion 32 of the front wall 18 slopes more substantially-down to the horizontal base 12. The inclined ramp 28 is capable of displaying indicia thereon. A set of locking members 40 is attached to the grooved tray 10 along one of the opposing sidewalls 16, allowing multiple grooved trays 10 to lock together and provide more holding space for the ring-handled surgical instruments.

Figure 2:
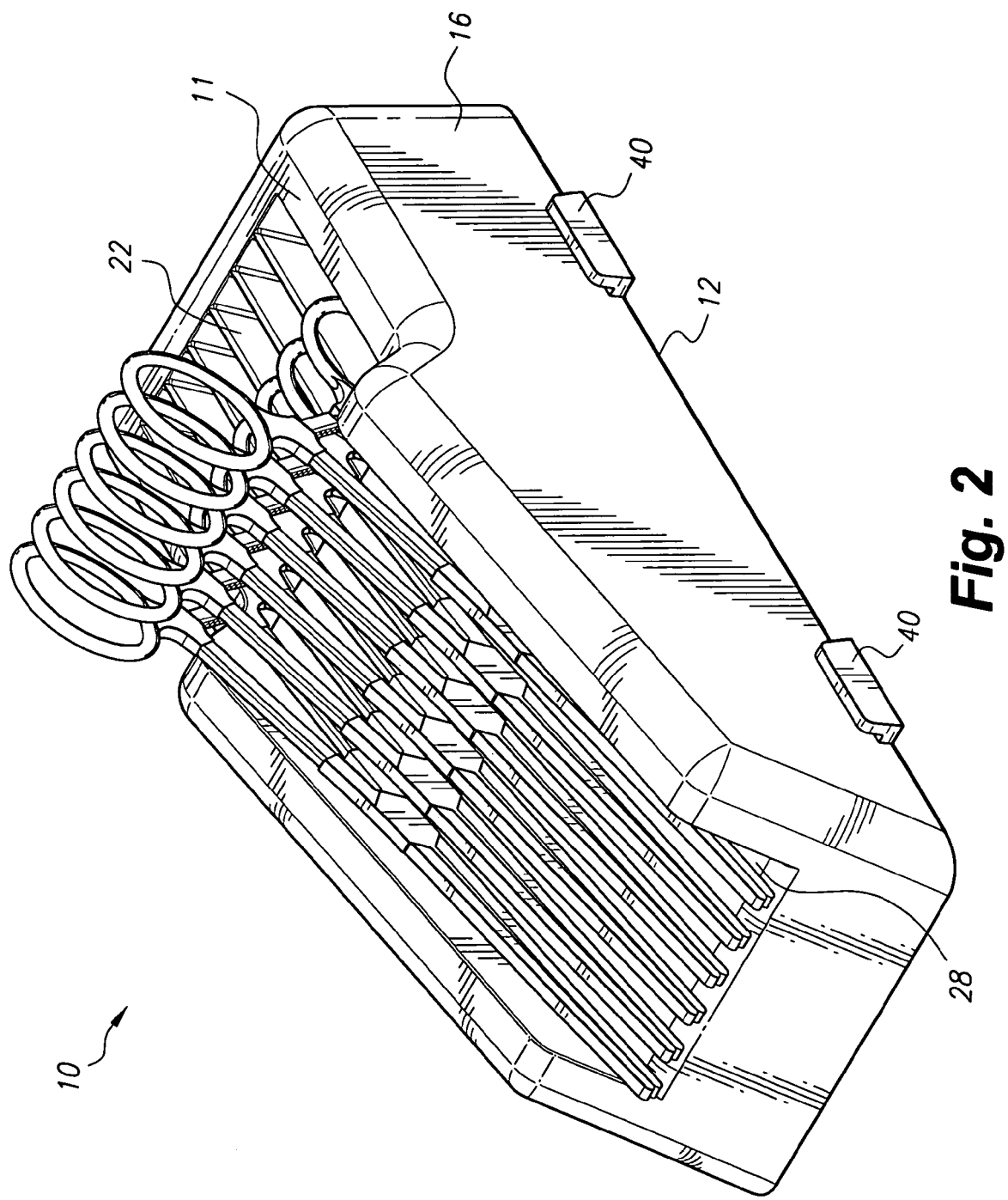
FIG. 2 is an environmental, perspective view of the grooved angled tray for ring-handled surgical instruments according to the first embodiment of the present invention with the surgical instruments mounted thereon.

As can be seen in FIG. 2, the grooves 22 and ramp 28 are adapted to hold and isolate multiple ring-handled instruments. The ring-handled instruments include, but are not limited to, snaps, Kellys, Ailises, Babcocks, Kochers, needle holders, sponge sticks, hemostats, forceps, and scissors. The ring-handled instruments can be separated by instrument type or instrument size. Portions of the ring handles of the ring-handled instruments are placed in the grooves 22. Lower portions of the instruments extend off of the edge of the inclined ramp 28, allowing a user to easily grip the instruments at ends of the instruments. The number of grooves 22 per tray 10 may be varied.

Figure 3:
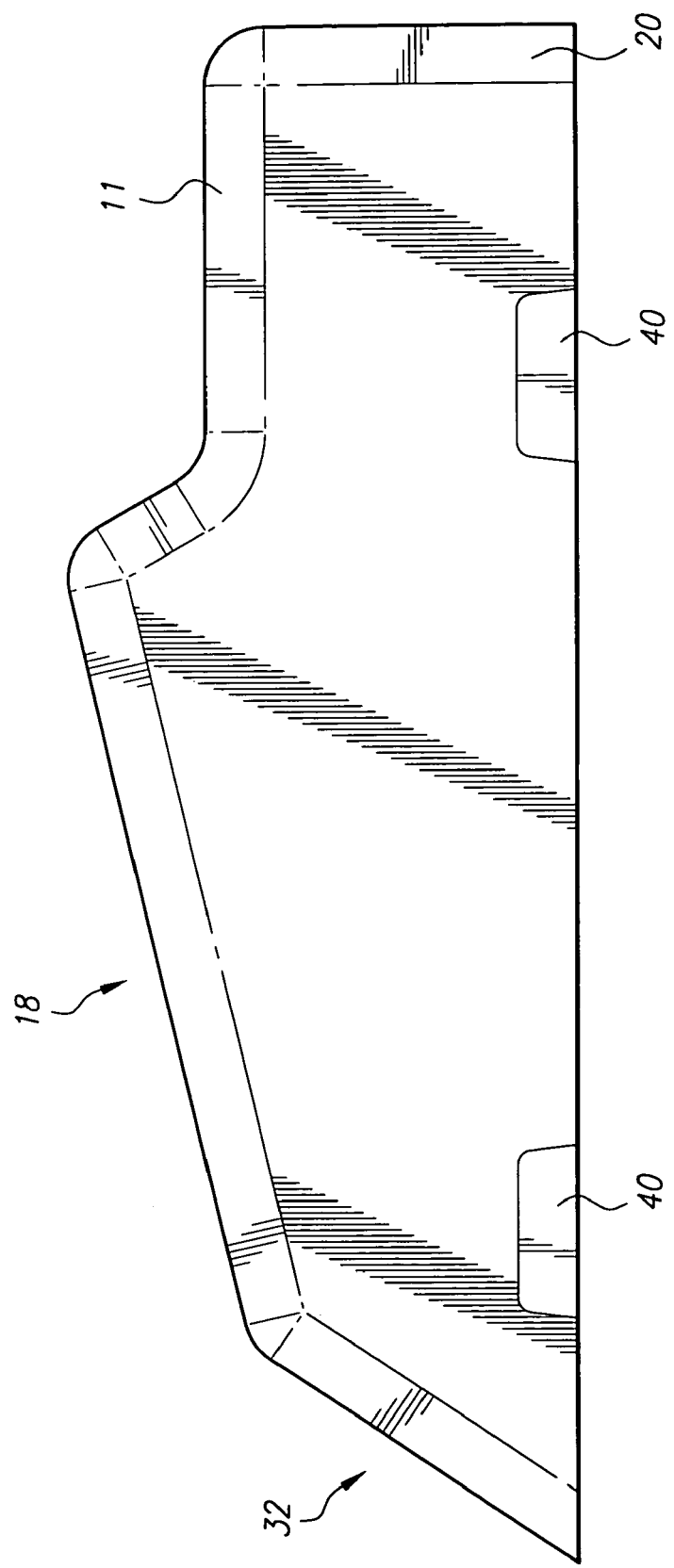
FIG. 3 is a section view along lines 3—3 of FIG. 1.

FIG. 3 shows a side view of the angled tray 10. The horizontal top 11 is disposed lower than the front wall 18. The portion of the front wall 18 that contains the ramp 28 inclines at a slight angle. The bottom portion 32 of the front wall 18 slopes at a greater angle to the base 12.

Figure 4:
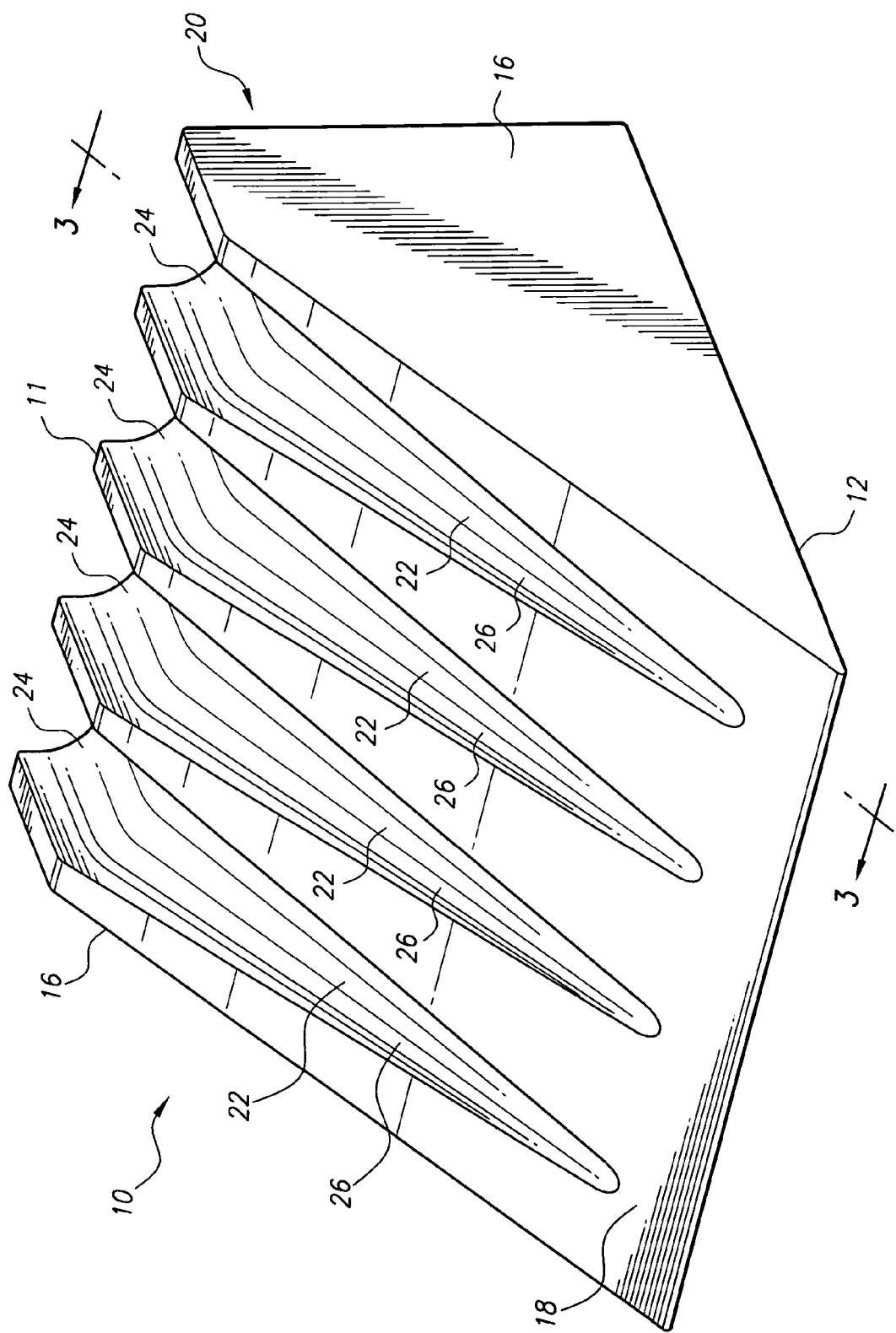
FIG. 4 is a perspective view of a grooved angled tray for ring-handled surgical instruments according to a second embodiment of the present invention.
Figure 5:
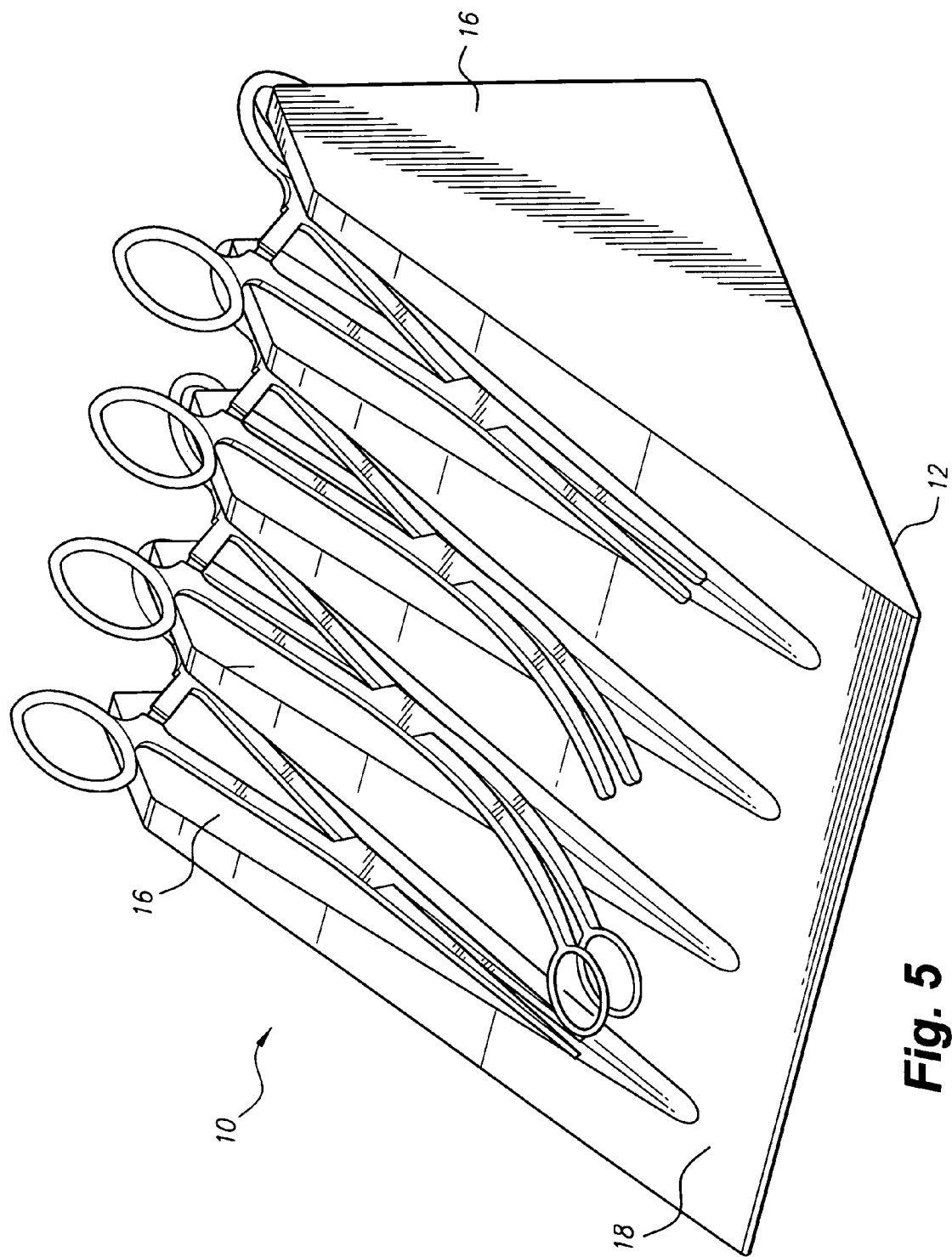
FIG. 5 is an environmental, perspective view of the grooved angled tray for ring-handled surgical instruments according to the second embodiment of the present invention with the surgical instruments mounted thereon.
Figure 6:
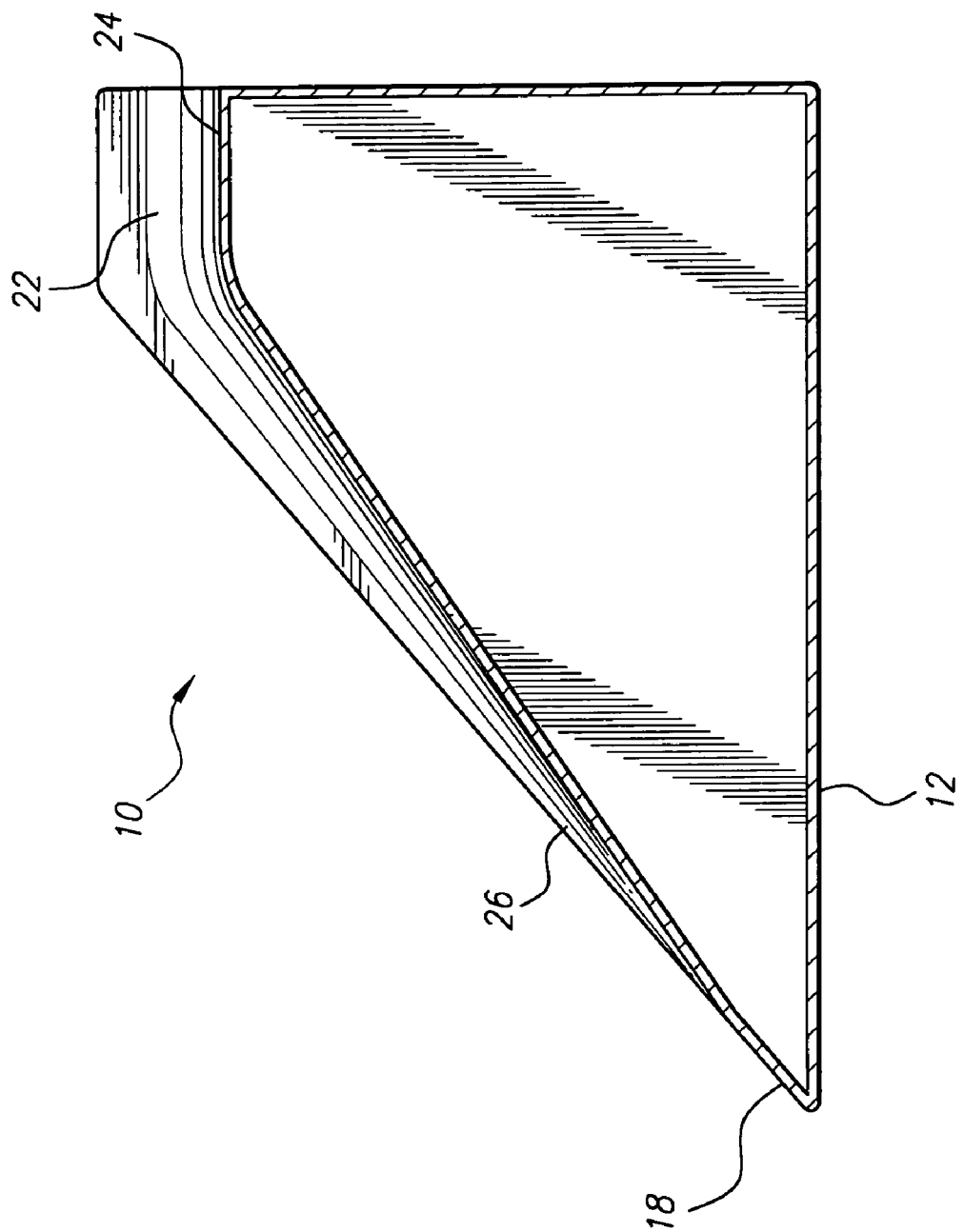
FIG. 6 is an elevational side view of the grooved angled tray for ring-handled surgical instruments according to the second embodiment of the present invention.

FIGS. 4–6 show an additional embodiment of the angled grooved tray 10. The horizontal top 11 is disposed higher than the front wall 18. The horizontal top 11 and the front wall 18 include a series of grooves 22. The grooves 22 extend from the horizontal top 11 to about the horizontal bottom 12. The grooves 22 substantially encompass the length of the horizontal top 11 and front wall 18. Preferably, each groove 22 has a horizontal upper portion 24 and an inclined lower portion 26. The groove lower portion 26 slopes outward from the groove upper portion 24. The number of grooves 22 per tray may vary.

As can be seen in FIG. 5, the grooves 22 are adapted to hold and isolate a variety of ring-handled instruments in the grooves 22 parallel to one another and in a slanted position. The groove upper portion 24 is configured to receive a portion of the ring handle. The groove lower portion 26 is configured to receive a lower portion of the ring-handled instrument.

As is more clearly shown in FIG. 6, each groove 22 is widest at the groove upper portion 24 and becomes progressively narrower along the groove lower portion 26. One ring handle of the ring-handled instruments extends over the horizontal upper portion 24 of the groove 22. The instruments, therefore, adopt a tilted orientation such that the handle is raised with respect to the remote, working end of the instruments.

The tray 10 is preferably made from one piece and is configured for positioning upon a back table or Mayo stand in a surgery room. If necessary, more than one tray 10 may be lined up together. The tray 10 can be made from any suitable material, including, but not limited to stainless steel and molded plastic. Preferably, the type of material used for the tray 10 is either one that can be easily sterilized or, alternatively, one that can be dispensed after use. Each tray 10 or each groove 22 within the tray 10 may be color-coded to further facilitate identification of the instruments.

It is to be understood that the present invention is not limited to the embodiment described above, but encompasses any and all embodiments within the scope of the following claims.

I claim:

1. A grooved angled tray for holding a plurality of ring-handled surgical instruments, each instrument having a ring handle and a lower portion, said tray comprising:
   a horizontal top having a front, a rear, and a pair of sides;
   a plurality of downwardly depending, elongate grooves in said horizontal top, said elongate grooves extending from the front to the rear of said top;
   a horizontal base parallel to said horizontal top, said horizontal base having a front edge, a rear edge and a pair of side edges;
   a vertical rear wall extending upwardly from said base rear edge to the rear of said horizontal top;
   first and second opposing sidewalls extending upwardly from the side edges of said base; and
   a front wall, said front wall including an inclined ramp and a bottom portion;
   said inclined ramp having an upper edge and a lower edge;
   said front wall bottom portion being inclined upwardly from the front edge of said base to said inclined ramp lower edge, and said inclined ramp being inclined upwardly from said lower edge to said upper edge;
   wherein said inclined ramp upper edge is located proximate to the front of said horizontal top and said horizontal top is disposed lower than the upper edge of said front wall inclined ramp.

2. The grooved angled tray for holding a plurality of ring-handled surgical instruments of claim 1, wherein said inclined ramp is substantially planar.

3. The grooved angled tray for holding a plurality of ring-handled surgical instruments of claim 1, wherein said inclined ramp has indicia displayed thereon.

4. The grooved angled tray for holding a plurality of ring-handled surgical instruments of claim 1, wherein said first and second sidewalls extend upwardly above said inclined ramp.

5. The grooved angled tray for holding a plurality of ring-handled surgical instruments of claim 1, including at least two locking members extending outwardly from said first sidewall and adjacent said base, said locking members configured to engage the second sidewall of another grooved angled tray,
   wherein a plurality of grooved angled trays may be assembled side-by-side, with the locking members on the first sidewall of one said plurality trays engaging the second sidewall of an adjacent tray.

* * * * *